(12) United States Patent
Unger

(10) Patent No.: US 11,534,492 B2
(45) Date of Patent: *Dec. 27, 2022

(54) FRACTIONATED RADIOTHERAPY AND CHEMOTHERAPY WITH AN OXYGEN THERAPEUTIC

(71) Applicant: NuvOx Pharma LLC, Tucson, AZ (US)

(72) Inventor: Evan C. Unger, Tucson, AZ (US)

(73) Assignee: NuvOx Pharma LLC, Tucson, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/169,484

(22) Filed: Feb. 7, 2021

(65) Prior Publication Data
US 2021/0260190 A1    Aug. 26, 2021

Related U.S. Application Data

(63) Continuation of application No. 16/550,183, filed on Aug. 24, 2019, now Pat. No. 10,946,097, which is a continuation of application No. 15/121,372, filed as application No. PCT/US2015/018942 on Mar. 5, 2015, now Pat. No. 10,456,468.

(60) Provisional application No. 61/948,406, filed on Mar. 5, 2014.

(51) Int. Cl.
| *A61K 41/00* | (2020.01) |
| *A61K 31/02* | (2006.01) |
| *A61K 33/00* | (2006.01) |
| *A61K 9/00* | (2006.01) |
| *A61K 9/107* | (2006.01) |
| *A61K 47/26* | (2006.01) |
| *A61N 5/10* | (2006.01) |
| *A61K 45/06* | (2006.01) |
| *A61K 39/395* | (2006.01) |
| *A61K 47/10* | (2017.01) |
| *A61K 47/24* | (2006.01) |
| *A61K 39/00* | (2006.01) |

(52) U.S. Cl.
CPC ........ *A61K 41/0038* (2013.01); *A61K 9/0019* (2013.01); *A61K 9/107* (2013.01); *A61K 31/02* (2013.01); *A61K 33/00* (2013.01); *A61K 39/395* (2013.01); *A61K 45/06* (2013.01); *A61K 47/10* (2013.01); *A61K 47/24* (2013.01); *A61K 47/26* (2013.01); *A61N 5/10* (2013.01); *A61K 2039/505* (2013.01); *A61K 2039/545* (2013.01); *A61N 2005/1098* (2013.01)

(58) Field of Classification Search
None
See application file for complete search history.

(56) References Cited

U.S. PATENT DOCUMENTS

| 10,456,468 B2 * | 10/2019 | Unger | A61K 47/10 |
| 10,946,097 B2 * | 3/2021 | Unger | A61K 39/395 |
| 2013/0096204 A1 * | 4/2013 | Johnson | A61K 31/025 |
| | | | 514/759 |

* cited by examiner

Primary Examiner — Melissa S Mercier
(74) Attorney, Agent, or Firm — Milstein Zhang & Wu LLC

(57) ABSTRACT

A fluorocarbon emulsion in water for use in fractionated radiotherapy and chemotherapy, wherein said fluorocarbon comprises between 4 and 8 carbon atoms.

16 Claims, 5 Drawing Sheets

FRACTIONATED RADIOTHERAPY AND CHEMOTHERAPY WITH AN OXYGEN THERAPEUTIC

PRIORITY CLAIMS AND RELATED PATENT APPLICATIONS

This application claims priority to and is a continuation of U.S. Ser. No. 16/550,183, filed Aug. 24, 2019, which claims priority to and is a continuation of U.S. Ser. No. 15/121,372, filed Aug. 24, 2016, which is the U.S. national phase of and claims priority to PCT/US2015/018942, filed Mar. 5, 2015, which claims the benefit of priority from U.S. Provisional Application Ser. No. 61/948,406, filed on Mar. 5, 2014, the entire content of each of which is incorporated herein by reference in its entirety.

FIELD OF THE INVENTION

The invention is directed to use of an oxygen therapeutic in combination with repeated administrations of chemotherapy medications and/or radiation therapy.

BACKGROUND OF THE INVENTION

A radiosensitizer is a drug that makes tumor cells more sensitive to radiation therapy. One of the major limitations of radiotherapy is that the cells of solid tumors become deficient in oxygen. Solid tumors can outgrow their blood supply, causing a low-oxygen state known as hypoxia. Oxygen is a potent radiosensitizer, increasing the effectiveness of a given dose of radiation by forming DNA-damaging free radicals. Tumor cells in a hypoxic environment may be 3 times more resistant to radiation damage than those in a normal oxygen environment.

BRIEF DESCRIPTION OF THE DRAWINGS

The invention will be better understood from a reading of the following detailed description taken in conjunction with the drawings in which like reference designators are used to designate like elements, and in which.

DETAILED DESCRIPTION OF PREFERRED EMBODIMENTS

Figure 1A:
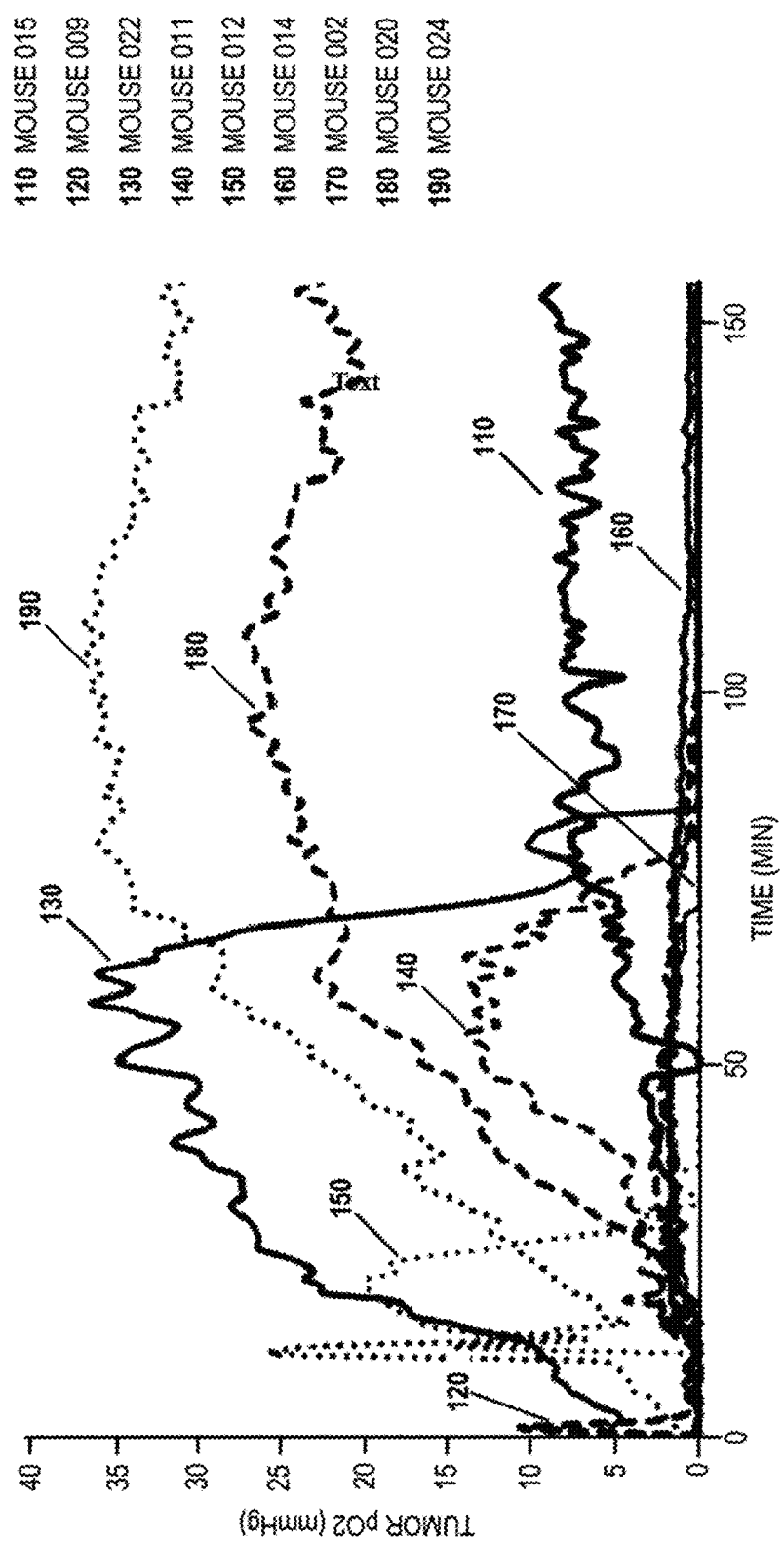
FIG. 1A graphically shows Oxygen levels in 9 Hs-766T pancreatic cancer tumor xenografts in mice. The different traces (lines) in all represent 9 tumors in 9 different mice. Each mouse was given a single dose of NVX-108: 0.3 mL/kg (blue traces), 0.45 mL/kg (green traces) or 0.6 mL/kg (red traces)
Figure 1B:
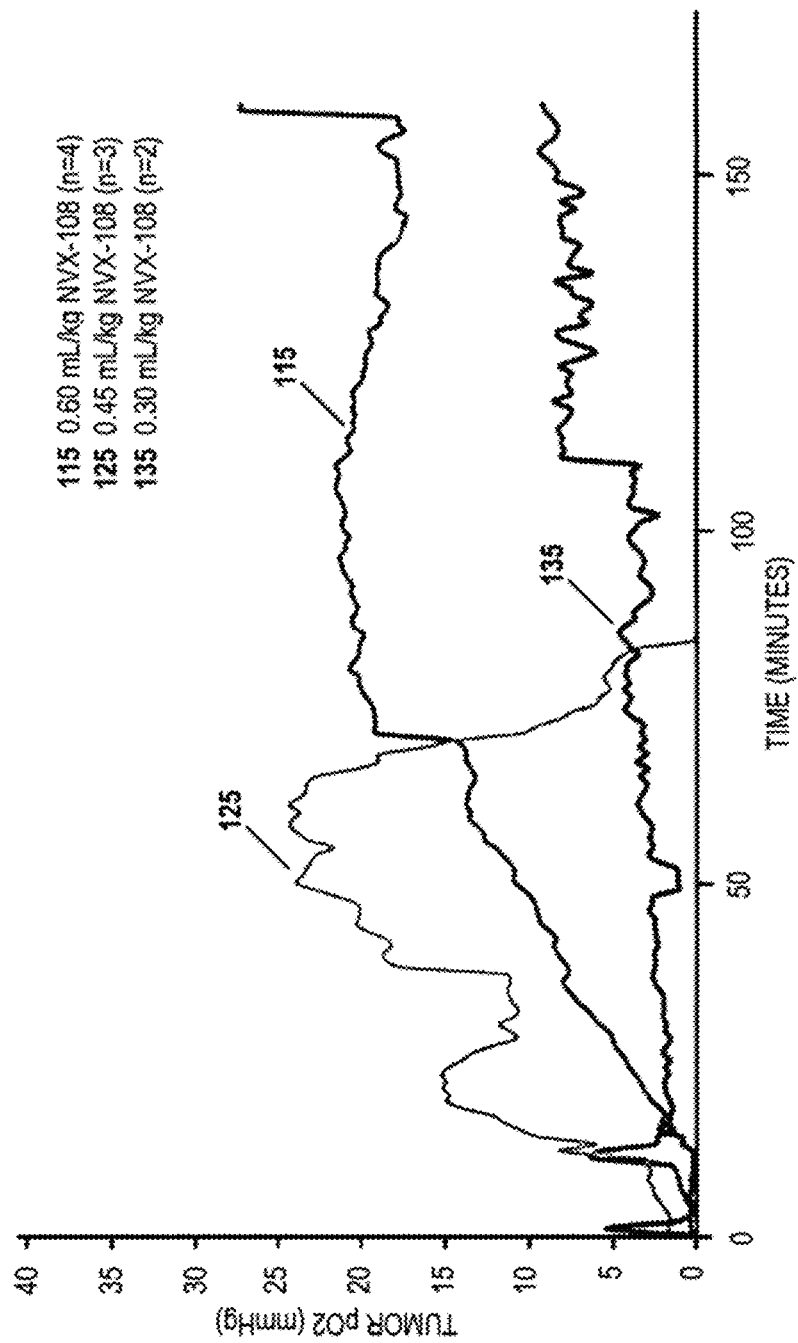
FIG. 1B graphically shows average and standard error oxygen levels in Hs-766T pancreatic cancer tumor xenografts in mice at the 3 different doses of NVX-108: 0.3 mL/kg (blue traces, n=2), 0.45 mL/kg (green traces, n=3) or 0.6 mL/kg (red traces, n=4)
Figure 2A:
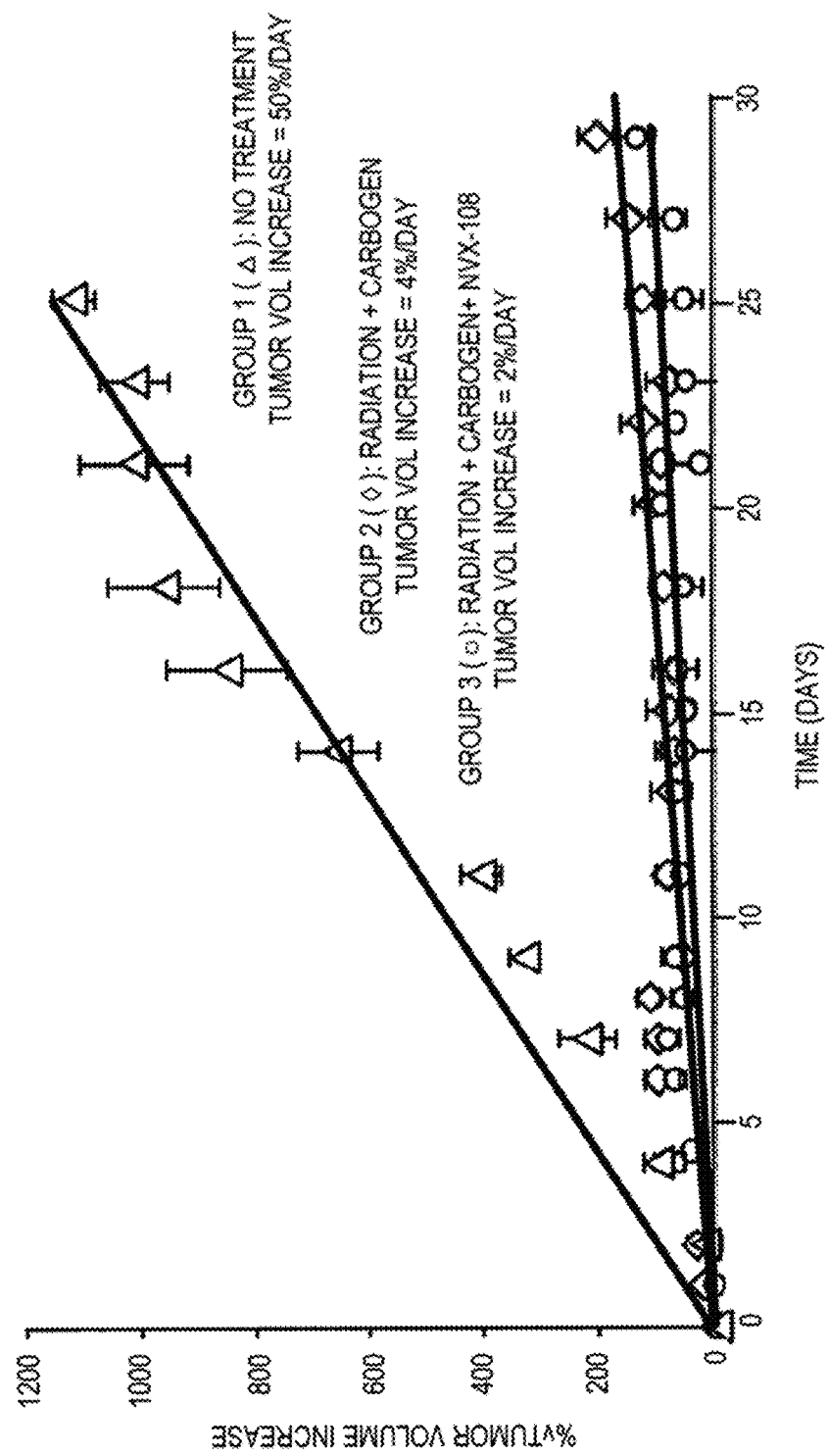
FIG. 2A graphically shows a comparison of percent tumor growth among 3 groups of mice.
Figure 2B:
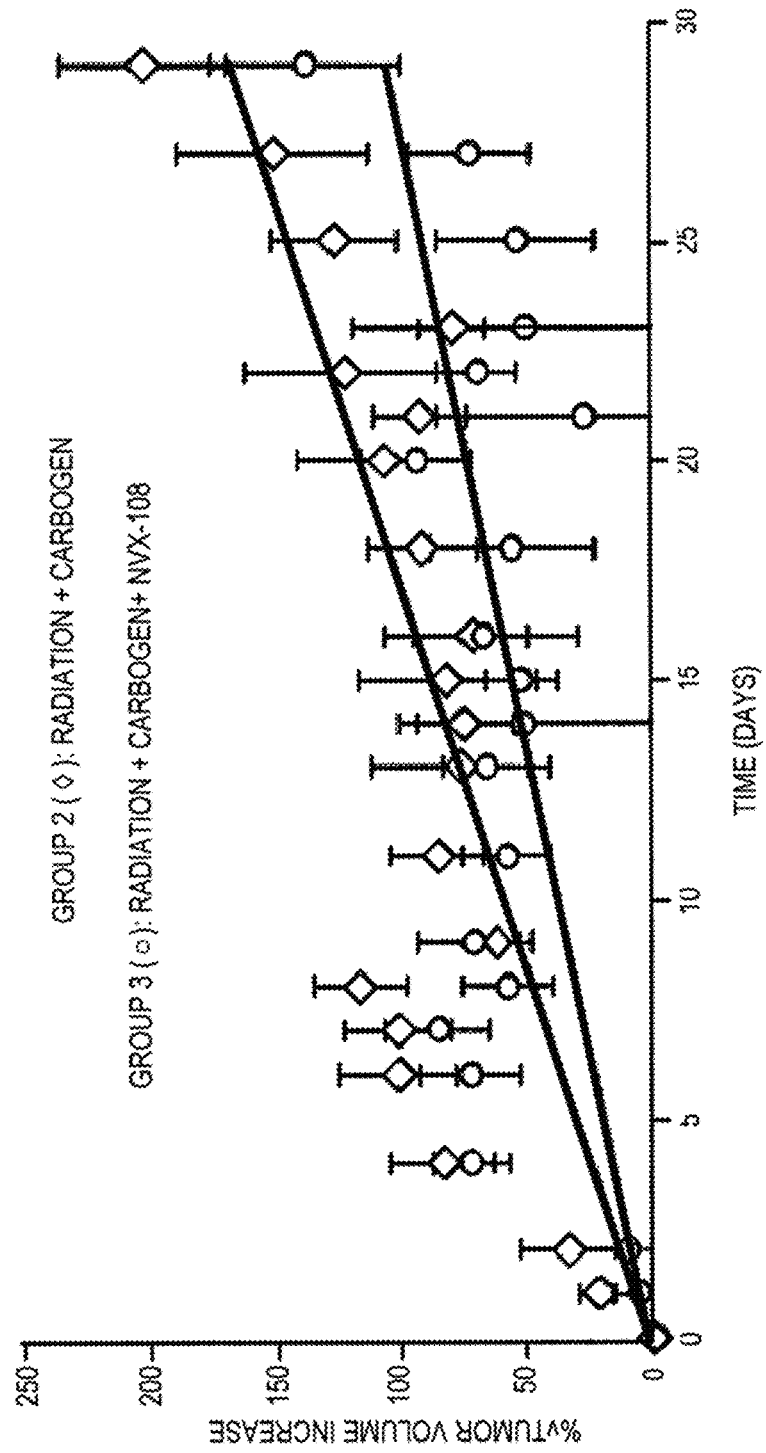
FIG. 2B is an expanded view of the two treated groups of FIG. 2A.
Figure 3:
FIG. 3 shows MRI scan images.
Figure 3:

This invention is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

Dodecafluoropentane emulsion (DDFPe) was previously tested as a sensitizer for radiotherapy with a single fraction of radiotherapy. Tumors (xenografts) were irradiated, the tumors removed from the animals, the cells disaggregated and tested for viability. Neither tumor growth nor survival was assessed and tumor $pO_2$ was not directly assessed. Nor were the effects of administration of DDFPe with chemotherapy assessed. Multi-dose administration of DDFPe with fractionated radiotherapy was not assessed.

In certain embodiments, the animal to be treated is a mammal. In certain embodiments, the animal to be treated is a human. In certain embodiments, doses range from about 0.01 cc/kg to about 1.0 cc/kg (2% w/vol DDFPe). In certain embodiments, the doses range from about 0.05 cc/kg to 0.3 cc/kg administered by infusion for up to 30 minutes or a single bolus. As one skilled in the art would recognize, if the concentration of DDFP in the emulsion is increased, e.g. to 5% or 10% by weight, the volume administered will generally be decreased accordingly. Preferably the subject is breathing oxygen or a mixture of oxygen and $CO_2$, e.g. carbogen, between 95% oxygen with 5% $CO_2$ to 98% oxygen with 2% $CO_2$. Applicant has discovered that use of carbogen and oxygen are comparable, but carbogen is problematic. It has to be ordered specially whereas oxygen is available everywhere.

DDFPe is administered IV prior to each fraction of radiation therapy. In certain embodiments, the DDFPe is administered as a product currently in clinical development under the name NVX-108.

In the prior art, relatively high molecular weight fluorocarbons have been studies as radiosensitizers. Materials that have been studied as radiosensitizers include F-1,3-dimethyladamantane, F-trimethylbicyclo[3.3.1]nonane, F-tributylamine (FC-43," 3M Company), perfluorodecalin and perfluorooctylbromide.

The inventor has discovered that lower molecular weight fluorocarbons (FC), most particularly with boiling points from about −4 degrees centigrade to about 100 degrees centigrade are far more effective than the higher molecular weight, higher boiling point FCs. More preferably the boiling point of the FC is from about 20 to about 80 degrees C. and still more preferably from about 28 degrees C. to about 60 degrees C. FCs useful in this invention include perfluorobutane, perfluoropentane, perfluorohexane, perfluoroheptane and perfluorooctane. Most preferred are perfluoropentane and perfluorohexane with the most preferred being perfluoropentane.

Most preferably the FC is prepared as an emulsion by high pressure, temperature controlled homogenization. A variety of surfactants may be used to prepare the emulsions. The preferred surfactants are phospholipids and a preferred composition of phospholipids includes dioleoylphosphatidylcholine (DOPC) and dioleoylphosphatidylethanolamine-PEG-5,000 (DOPE-PEG 5 k). Another preferred mixture of phospholipids include dipalmitoylphosphatidylcholine (DPPC), and dipalmitoylphosphatidylethanolamine-PEG-5,000 (DPPE-PEG 5 k). A preferred ratio of lipids is 92 mole percent DPPC with 8 mole percent DPPE-PEG. The same ratio of lipids is also preferred for the unsaturated phosphatidyl moieties. Other lipids such as cholesterol, phosphatidic acid, stearic acid, palmitic acid, oleic acid and phosphatidylethanolamine may be mixed with the above mentioned lipids. Other useful surfactants include fluorosurfactants such as PEG Telomer B and CAPSTONE (DuPont). Mixtures of phospholipids and the fluorosurfactants may be used. Other surfactants include polyoxyethylene-polyoxypropylene copolymer surfactant e.g. "Pluronic" F-68.

Preferably a viscogen is included in the formulation to increase the viscosity in the product to decrease settling of the nano-emulsion. Viscogens include sucrose, carboxymethylcellulose, trehalose, starch, Hextend®, xanthan gum, propylene glycol, glycerol and polyethylene glycol ranging in molecular weight from about 400 to 8,000 MW. Preferably the formulation also includes a buffer such as sodium phosphate to stabilize the pH near neutrality, i.e. pH=7.0.

Because of the greater efficacy of the present invention using the lower boiling point FCs much lower doses can be administered to effectively reverse radiation resistance. For example, NVX-108 only has 2% w/vol DDFP. Prior materials had >10% w/vol FC. For this invention the preferred weight range is from about 1% to 5% w/vol FC with 2% w/vol FC most preferred, e.g. 2% w/vol DDFP or perfluorohexane.

Experiments in animals bearing tumor xenografts showed that the effects of NVX-108 on tumor $pO_2$ were comparable on animals breathing carbogen and oxygen. But the effect on tumor $pO_2$ was less in animals breathing room air. Therefore for the purpose of this invention the subject may breathe either carbogen or supplemental oxygen during and/or after administration of the emulsion and during radiotherapy or administration of chemotherapy.

The material may be administered concomitantly with radiotherapy or prior to radiotherapy, e.g. up to about 120 minutes prior to radiotherapy. Optionally, in addition to radiotherapy, or alone, chemotherapy is administered concomitantly with DDFPe. A variety of anti-neoplastic agents may be employed in the invention including but not limited to alkylating agents, antimetabolites, anthracyclines, topoisomerase inhibitors, mitotic inhibitors, corticosteroids, miscellaneous chemotherapy drugs, targeted therapies, hormone therapy and immunotherapy.

NVX-108 comprises a formulation having the components recited in Table 1.

As a general matter, Applicant's fluorocarbon emulsion does not comprise any amidoamine oxide compounds. More specifically, Applicant's fluorocarbon emulsion does not comprise any fluorinated amidoamine oxide compounds.

Alkylating agents include but are not limited to nitrogen mustards: such as mechlorethamine (nitrogen mustard), chlorambucil, cyclophosphamide (Cytoxan®), ifosfamide, and melphalan; nitrosoureas: which include streptozocin, carmustine (BCNU), and lomustine; alkyl sulfonates: busulfan; triazines: dacarbazine (DTIC) and temozolomide (TEMODAR); ethylenimines: thiotepa and altretamine (hexamethylmelamine). The platinum drugs (cisplatin, carboplatin, and oxalaplatin) are sometimes grouped with alkylating agents because they kill cells in a similar way.

Examples of antimetabolites include: 5-fluorouracil (5-FU), 6-mercaptopurine (6-MP), capecitabine (XELODA), cladribine, clofarabine, cytarabine (ARA-C), floxuridine, fludarabine, gemcitabine (GEMZAR), hydroxyurea, methotrexate, pemetrexed (ALIMTA), pentostatin and thioguanine. Anthracyclines include: daunorubicin, doxorubicin (ADRIAMYCIN) and epirubicin. Idarubicin anti-tumor antibiotics that are not anthracyclines include: actinomycin-bleomycin, and mitomycin-C. Mitoxantrone is an anti-tumor antibiotic that is similar to doxorubicin in many ways. Examples of topoisomerase I inhibitors include topotecan and irinotecan (CPT-11). Examples of topoisomerase II inhibitors include etoposide (VP-16) and teniposide. Mitoxantrone also inhibits topoisomerase II. Examples of mitotic inhibitors include: taxanes: paclitaxel (TAXOI) and docetaxel (TAXOTERE). Epothilones include ixabepilone (IXEMPRA). Vinca alkaloids include vinblastine (VELBAN), vincristine (ONCOVIN), and vinorelbine (NAVELBINE) and estramustine (EMCYT). Examples of corticosteroids include prednisone, methylprednisolone (SOLUMEDROL), and dexamethasone (DECADRON). Examples of targeted therapies include imatinib (GLEEVEC), gefitinib (IRESSA), sunitinib (SUTENT) and bortezomib (VELCADE).

Examples of differentiating agents include the retinoids, tretinoin (ATRA or ATRALIN) and bexarotene (TARGRETIN), as well as arsenic trioxide (ARSENOX). Examples of hormone therapy agents include the anti-estrogens: fulvestrant (FASLODEX), tamoxifen, and torcmifene (FARESTON). Aromatase inhibitors include: anastrozole (ARIMIDEX), exemestane (AROMASIN), and letrozole (FEMARA). Progestins include megestrol acetate (MEGACE) and estrogens. Anti-androgens include bicalutamide (CASODEX), flutamidc (EULEXIN), and nilutamde (NILANDRON). Gonadotropin-releasing hormone (GnRH), also known as luteinizing hormone-releasing hormone (LHRH) agonists or analogs include leuprolide (LUPRON) and goserelin (ZOLADEX).

TABLE 1

| INGREDIENT | SPECIFICATION | PURPOSE | CONC (MG/ML) |
| --- | --- | --- | --- |
| DODECAFLUOROPENTANE | MEDICAL GRADE | ACTIVE | 20 |
| SUCROSE | MEDICAL GRADE | EXCIPIENT | 300 |
| PEG TELOMER B | PURIFIED CHEMICAL GRADE | EXCIPIENT | 3 |
| WATER FOR INJECTION | USP | SOLVENT | Q.S. TO 1 ML |
| NITROGEN | MEDICAL GRADE | HEAD SPACE AIR FLUSH | Q.S. |
| SODIUM PHOSPHATE | USP | BUFFER | 0.01M |
| HYDROCHLORIC ACID | USP | EXCIPIENT | Q.S. |

Types of immunotherapies and some examples include: monoclonal antibody therapy (passive immunotherapies), such as rituximab (RITUXAN) and alemtuzutnab (CAMPATH). Non-specific immunotherapies and adjuvants (other substances or cells that boost the immune response) include BCG, interleukin-2 (IL-2), and interferon-alfa. Immunomodulating drugs, for instance, thalidomide and lenalidomide (REVLIMID). Cancer vaccines (active specific immunotherapies such as PROVENGE vaccine for advanced prostate cancer may be used with DDFPe and other vaccines currently under development. Administration of the FC increases the activity of the immunotherapy, for example Yervoy® (Ipilimumab) as the immune cells are more active in an oxidative environment achieved through tumor re-oxygenation. Other immune modulating drugs that can be used with the FC emulsions include Inhibitors of PD-L1 expression. Monoclonal antibodies are particularly useful with the invention. The antibodies can be used as vaccines to trigger an immune response to reject the cancer. Non-specific stimulators of the immune system can be used in the invention. Examples include cytokines such as interleukins and interferons such as Interferon-alpha and Interleukin-2: Antibodies useful in this invention include Alemtuzumab, Bevacizumab, Brentuximab vedotin, Cetuximab, Gemtuzumab ozogamicin, Ibritumomab tiuxetan, lpilimumab, Nivolumab, Ofatumumab, Panitumumab, Rituximab, Tositumomab and Trastuzumab. The invention can be used with Adoptive T-cell therapy Anti-CD47 antibodies, Anti-GD2 antibodies, Immune checkpoint blockade and EGF receptor antibodies. Administration of the emulsion can be used to increase the oxygen in the tumor tissue so that immune mechanisms accelerated of oxidative stress through increasing oxygen and making the immune system more efficient but also by changing gene expression. By decreasing expression of hypoxia related genes the oxygen therapeutic converts the aggression hypoxia mediated phenotype to a less aggressive phenotype that is more easily defeated by the immune system. In certain embodiments, Applicant's invention includes a method to alter gene expression by administering to a patient in need thereof, a therapeutically effective dosage of an oxygen therapeutic, such as and without limitation, NVX-108.

Administration of DDFPe, preferably while breathing supplemental oxygen, or carbogen, increases tumor oxygenation, enabling the chemotherapeutic drugs to work more effectively. Synergy is furthermore attained by simultaneous radiotherapy.

The following examples are presented to further illustrate to persons skilled in the art how to make and use the invention. These examples are not intended as a limitation, however, upon the scope of the invention.

Example 1

Preparation of Dodecafluoropentane Emulsion

A 30% sucrose solution was prepared by dissolving appropriate amount of USP grade sucrose in water for injection at room temperature followed by sodium dihydrogen phosphate to buffer the system at a pH of 7.0. In a second vessel a suspension of DDFP (dodecafluoropentane) in Peg Telomer B in the ratio of DDFP:PEG Telomer B: 7:1 (w:w), was prepared as follows. PEG Telomer B was dispersed in water for injection by stirring in a jacketed vessel cooled to 4° C. Pre-cooled (4° C.) DDFP was added to the stirred PEG Telomer B and allowed to stir until a uniformly milky suspension was achieved. This suspension was homogenized under high pressure in an Avestin model C50 homogenizer for up to 18 minutes keeping the temperature below 7° C.). The emulsion was transferred via the homogenizer under low pressure to a vessel containing 30% sucrose solution in water; the resulting solution was stirred for up to 20 minutes, and then transferred through the homogenizer under low pressure to a second vessel. This solution was then transferred through a 0.2 micron filter into a third vessel. The product was dispensed to vials, which were capped and crimped. These operations were carried out at <8° C. in cold jacketed vessels due to the volatility of the active ingredient (DDFP). Compensation for losses during processing were accounted for by the use of an overage of the active component. Product fill volume was also tightly controlled to produce vials to meet release and shelf-life specifications. The resulting product comprised 2% w/vol DDPE. Particle sizing by Nycomps showed mean particle size of about 250 nm.

Example 2

An experiment was performed in Hs-766t pancreatic cancer xenografts implanted in mice. The Hs-766T (pancreatic; ATCC Cat #HTB-134) cell line utilized for this study was obtained from the American Type Culture Collection (ATCC, Manassas, Va.) and was handled, stored and managed by the University of Arizona Experimental Mouse Shared Services (EMSS, University of Arizona). Cells were grown in DMEM (Mediatech) with high glucose, L-glutamine and 10% fetal bovine serum and maintained at 37°C. with 5% $CO_2$. Tumor cells were authenticated through ATCC Cell Authentication testing services by way of PCR/ short tandem repeat (STR) profiling. Cells were routinely tested for *mycoplasma* using the Universal Mycoplasma Detection Kit (ATCC, 30-1012K), and found to be free of contamination.

Twenty-nine female, SCID mice between the ages of 5-8 weeks of age were used in these studies. All mouse feeding, husbandry and veterinary was managed by the EMSS under IACUC approved guidelines and protocols. Mice were caged in groups of four or less, and fed and watered ad libitum. Prior to injection, mice were shaved to ascertain a suitable site for the tumor xenografts. Tumor cells ($10\times10^6$ cells in Matrigel™; BD Bioscience) were injected subcutaneously on the left rear flank of each mouse. Tumor burden evaluations were made twice weekly using electronic calipers to determine tumor size ($(a2\times b2)/2$). When tumors reached a mean volume of 500-700 $mm^3$ the mice were randomized to one of 6 groups: 3 groups of mice for tumor $O_2$ measurements and 3 groups of mice for tumor growth measurements.

Tumor $pO_2$ measurements were performed in 9 of the mice. NVX-108 doses of 0.3 (2 mice), 0.45 (3 mice) and 0.6 (4 mice) mL/kg (2% w/vol emulsion) were administered. Tumor growth rate was studied in the other 20 mice. These mice were designated to the following 3 treatment groups: Group 1: No treatment (4 mice), Group 2: breathing carbogen while being treated with a 12 Gy radiation dose (8 mice), Group 3: Treated with NVX-108 (0.6 cc per kg, 2% w/vol dodecafluoropentane (DDFP) administered IV over 30 minutes with radiation at end of infusion) and breathing carbogen while being treated with a 12 Gy radiation dose (8 mice).

Each mouse received ketamine (20 mg/kg IP) with xylazine (5 mg/kg IP) for immobilization and was fitted with a tail-vein catheter for dosing by tail vein injection (TVI). The tail-vein catheterization was achieved by using a fabricated 27-gauge needle catheter retrofitted to PE 50 tubing. The catheter was firmly affixed to each animal's tail using 3-0 suture thread and specialized adhesive tape on both sides of the tail. Following catheterization, the mice were placed within a custom-built gas chamber introducing carbogen (95% $O_2$, 5% $CO_2$) which was ventilated at the 10-minute mark. They were held in custom restraints in order to be positioned under a lead shield isolating the flank tumor xenograft for radiation fractionation. All mice underwent a single fractionation of 12 Gy to the tumor within a custom-built gas chamber introducing carbogen (95% $O_2$, 5% $CO_2$) which was ventilated at the 10-minute mark. The calculation for the XRT dose duration was based on "prescribed dose/dose rate"=(1200 cGy)/(87.9 cGy/min) amounts to a 13.65 minute (13 m39 s) single fraction delivered to the tumor. For group #2, 200 μL sterile saline was introduced via tail vein injection (TVI) (Time 0:00) and served as the sham injection commencing 10 minutes prior to carbogen breathing and 16.35 minutes (16 m21 s) before irradiation. For group #3, 200 μL of NVX-108 was injected by way of TVI (Time 0:00) 10 minutes before carbogen breathing and 16.35 minutes before irradiation. Tail vein injections were performed with a multi-syringe pump for simultaneous administration to each group. Simultaneous injections of NVX-108 and saline initiated the study at time 0:00 minutes. This was followed by carbogen breathing at 10 minutes and then radiation at 16.35 minutes.

Once radiation was completed, the mice were allowed to recover and have food and water ad libitum. Tumor size bi-dimensional measurements were performed twice per week. When tumor size was greater than 2000 mm3, mice were sacrificed.

Tumor oxygenation and blood flow levels were monitored using OxyLab (Oxford Optronics, Oxford, UK) triple parameter E-series fiber-optic probes stereotactically inserted into all tumors. Oxygen partial pressure signals from these monitors were recorded in real-time using a multi-channel data acquisition system (PowerLab 8SP, ADInstruments, Australia) running under Chart™ for Windows™ (Ver.5.02, ADInstruments, Australia). Anesthetized mice (Isoflurane®), 100% $O_2$) were restrained on a custom immobilization platform to prevent movement and retrofitted with a heating pad to sustain body core temperature. Precaution was taken to prevent any movement of the hypoxia probes and eliminate interference from external light sources to prevent probe artifact. Tumors were penetrated using a 19 gauge needle to a depth of ~2-4 mm and microprobes (OD ~450 μm) were fed through the needle into the tumor xenografts and fixed in position using stereotactic methods. Microprobes were carefully marked with gradations in order to reach the same depth in all tumors. Once the probes were stabilized and immobilized the output signals were monitored (5-10 min) until a stable baseline was observed. Real-time measurements were taken for 10 minutes at baseline on carbogen and following a 200 μL IV injection via tail vein of doses of 0.3, 0.45 or 0.6 cc/kg NVX-108 (NuvOx Pharma Tucson, Ariz.) while animals continued to breathe carbogen.

Example 3

Treatment of Glioblastoma Multiforme (GBM)

A patient with GBM undergoes surgery. The post-surgery gadolinium enhanced MRI scan shows residual enhancing tumor. The patient is treated with 30 fractions of radiotherapy of 2 Gray (Gy) each over 6 weeks for a total of 60 Gy with oral administration of temozolamide day, at a dose of 75 mg per square meter per day given 7 days per week from the first day of radiotherapy until the last day of radiotherapy. The patient receives an intravenous PICC line. DDFPe is administered at a dose of 0.05 cc/kg (2% w/vol) as IV infusion over 30 minutes with infusion commencing about 30 minutes prior to initiation of each radiotherapy session. Magnetic resonance TOLD scan is performed to show reversal of tumor hypoxia.

Follow-up MRI scans performed with intravenous gadolinium contrast show decrease in tumor compared to patients treated without DDFPe.

Baseline post-operative MRI scan is shown hereinbelow to left. White arrow designates residual enhancing tumor seen in medial left temporal lobe. Scan to right is 4 weeks after completion of chemo-irradiation and treatment with DDFPe. White arrow designates residual enhancing tumor. Enhancing tumor has decreased by about 80%. Patient is now alive and doing well more than 6-months after completion of therapy.

Example 4

Treatment of Glioblastoma Multiforme (GBM)

Another patient with glioblastoma undergoes surgery and has residual tumor visualized on contrast enhanced MRI. The patient is treated as in Example 1 (above) except using a dose of 0.1 cc/kg of DDFPe. The patient tolerates the treatment well. The next patient, presently being consented will be treated with a dose of 0.17 cc/kg of DDFPe during each fraction of chemo-irradiation.

Prophetic Example 1

A patient with non-small cell lung cancer is treated with thoracic radiotherapy and concomitant chemotherapy as described by the protocol by Belani, et al. "Sequential chemotherapy consisted of two 3-week cycles of paclitaxel 200 mg/m$^2$ administered over 3 hours, immediately followed by carboplatin at an area under the plasma concentration time curve (AUC)=6 mg/mL·min as an intravenous infusion over 30 minute. Thoracic radiotherapy is initiated on day 42 and consists of 1.8 Gy daily, five times per week (45.0 Gy target dose in 5 weeks to the initial field), followed by a total of 18.0 Gy fractions delivered at 2.0 Gy fractions daily to the initial tumor volume with reduced fields (total dose, 63.0 Gy in 34 fractions over 7 weeks), but including enlarged lymph nodes ≥2.0 cm.3" DDFPe is administered IV as an infusion over 15 minutes, commencing 30 minutes before the initiation or radiotherapy (RT), for each fraction of RT. Patients treated with DDFPe show improved response to the regimen.

Prophetic Example 2

A patient with Stage I non-small cell lung cancer is treated with a hypo-fractionated radiotherapy schedule with three fractions of 15 Gy to a total of 45 Gy during 1 week. This represents a biological equivalent dose (BED) of 112.5 Gy. Between 30 to 60 minutes prior to each radiation dose, the patient is administered a bolus IV dose of 0.17 cc/kg NVX-108 (2% w/vol DDFPe). Follow-up shows greater eradication of the treated tumor than would be observed without DDFPe.

Prophetic Example 3

A female patient with cervical carcinoma is treated with combined radiation therapy and chemotherapy+NVX-108.

Radiation dosage is 45 Gray (Gy) in 20 fractions followed by low dose-rate intracavitary application of 30 Gy to the cervical region. Chemotherapy consists of intravenous cisplatin 40 mg/m2 every week for up to 6 weekly cycles. The patient is administered a bolus IV dose of 0.2 cc/kg NVX-108 (2% w/vol DDFPe) 60 minutes prior to each dose of radiation. Follow-up shows complete response to treatment.

Prophetic Example 4

A patient with squamous cell carcinoma of the head and neck is treated with 0.50 units/kg (20 units/m2) of bleomycin intravenously twice weekly. During each administration of bleomycin the patient is administered 0.2 cc/kg of 2% w/vol perfluorohexane emulsion while breathing carbogen (98% $O_2$/2% $CO_2$). The increased oxygen levels attained in the tumor tissue increase the activity of the bleomycin and an improved response is attained.

Prophetic Example 5

An adult patient with germ cell ovarian cancer is treated with dactinomycin 500 mcg/day for 5 day: every 4 weeks. Each vial of dactinomycin contains 0.5 mg (500 meg) of dactinomycin and 20 mg of mannitol and is administered IV to the patient. DDFPe (0.2 cc/kg, 2% w/vol DDFP) is infused as an IV bolus concomitantly with each administration of dactinomycin. The patient breathes carbogen for 30 minutes during and after the infusion. Increased levels of oxygen in the tumor tissue are attained, enhancing the activity of the drug.

Prophetic Example 6

An adult patient with rhabdomyosarcoma is treated with IV Vincristine at a dose of 1.4 mg/m2. Concomitantly the patient is administered 0.1 cc kg of DDFPe while breathing room air. Despite breathing room air, increased oxygen levels am still attained in the tumor tissue resulting in increased activity of the drug.

Prophetic Example 7

A patient with multiple myeloma is treated with BiCNU® (carmustine for injection), a nitrosourea (1,3-bis(2-chloro-1-nitrosourea) in combination with prednisone. The dose of BiCNU administered to this previously untreated patient is 200 mg/m2 intravenously every 6 weeks. This is divided into daily injections of 100 mg/m2 on 2 successive days. DDFPe is administered as an IV bolus (dose=0.2 cc/kg, 2% w/vol DDFP) during each dose of BiCNU while the patient breathes supplemental oxygen for 60 minutes. A repeat course of BiCNU is again administered once the circulating blood elements have returned to acceptable levels (platelets above 100,000/mm3, leukocytes above 4,000/mm3), in 6 weeks, and again DDFPe is administered concomitantly with BiCNU.

Prophetic Example 8

A patient with prostate cancer is treated with combination external beam radiotherapy and high temporary seed implant high dose rate brachytherapy. About 3 weeks after receiving 45Gy of external beam radiotherapy for prostate cancer temporary seed implant with high dose rate brachytherapy is performed. The patient is brought to the operating room and anesthesia is induced. A transrectal ultrasound probe is introduced into the rectum and the probe is then secured into a floor mounted stepping device. A needle guide/perineal template is attached to the stepping unit and pushed up against the perineal skin. Twenty metal needles are placed through the template, pushed through the perineum, and advanced to the mid-prostate gland. The needles are replaced with plastic catheters. Upon recovery, the patient is brought to the Radiation Oncology department. CT scanning is performed to confirm the accuracy of the catheter placements. This computer-controlled high dose radiotherapy unit contains a source drive mechanism that moves the radioactive Iridium wire through the interstitial catheters sequentially in accordance with the loading pattern determined by the dosimetry plan. It takes about 10-15 minutes for the high dose rate brachytherapy procedure to be performed wherein the iridium wire is advanced into each of the interstitial catheters. This is repeated one more time and the patient is transferred to the hospital room for 6-hours, and the process is repeated again, for two more high dose rate brachytherapy administrations, e.g. the iridium wire is advanced into each catheter a total of four times, twice in the morning and twice in the afternoon, each session taking a total of about 30-minutes. During each treatment session the patient is administered a bolus dose of 0.2 cc/kg DDFPe over 30 minutes while breathing carbogen. http://prostate-cancer.org/temporary-seed-implant-with-high-dose-rate-brachytherapy/

Prophetic Example 9

A pediatric patient with Stage IV Wilms tumor is treated with dactinomycin, doxorubicin, cyclophosphamide and vincristine for 65 weeks. Doses of the drugs are as follows: dactinomycin (15 mcg/kg/d [IV]), vincristine (1.5 mg/m 2 wk [IV)), Adriamycin (doxorubicin 20 mg/m 2/d [IV]), and cyclophosphamide (10 mg/kg/d [IV]). Dactinomycin courses are given postoperatively and at 13, 26, 39, 52, and 65 weeks. Vincristine is given on days 1 and 8 of each Adriamycin course. Adriamycin is given for three daily doses at 6, 19, 32, 45, and 58 weeks. Cyclophosphamide is given for three daily doses during each Adriamycin and each dactinomycin course except the postoperative dactinomycin course. During each administration of dactinomycin and vincristine a dose of 0.2 cc/kg of DDFPe is administered while the patient breathes supplemental oxygen. * D'angio, Giulio J., et al. "Treatment of Wilms' tumor. Results of the third national Wilms' tumor study." Cancer 64.2 (1989): 349-360.

Prophetic Example 10

A patient with unrespectable hepatocellular carcinoma is under treatment with sorafenib. The patient is receiving 400 mg per day of oral sorafenib (2×200 mg). In a single setting the patient is also treated with TheraSphere which consists of insoluble glass microspheres where yttrium-90 is bound within the spheres. The hepatic artery is catheterized and the tumor vascular bed is embolized with TheraSphere delivering a target dose of TheraSphere of 100 Gy by injection through the hepatic artery. A dose of 0.1 cc per kg of DDFPe is mixed with oxygen and is also infused into the hepatic artery during the embolization procedure.

Prophetic Example 11

Xenograft tumors were generated in mice with cell lines of UTSCC33 (oral carcinoma), FADUDD (a subline of FaDu, an undifferentiated hypopharyngeal carcinoma) and SiHa uterine cervix carcinoma. HPV-positive, (obtained from the American Type Culture Collection) as previously described. See, Toustrup, Kasper, et al. "Development of a hypoxia gene expression classifier with predictive impact for hypoxic modification of radiotherapy in head and neck cancer." Cancer research 71.17 (2011): 5923-5931 (hereinafter "Toustrup").

Mice bearing each kind of tumor were randomly assigned to two groups, DDFPe treatment and control (injected with same volume of saline). DDFPe treatment comprised administration of 0.3 cc/kg of DDFPe IV as bolus each day for 14 days. After the 14th day the mice were sacrificed and the tumors assayed for expression of hypoxia related genes. See, Toustrup RNA from fresh-frozen tissue was extracted by using RNeasy-kit (Qiagen) according to the manufacturer's instructions. cDNA was generated by using the High Capacity cDNA Archive kit (Applied Biosystems; ABI) and gene expression was quantified by using qPCR. cDNA based on FFPE samples was preamplified according to the manufacturer's details (TaqMan PreAmp, ABI) before real time qPCR. To detect transcripts of interest, TaqMan Gene Expression assay (ABI) was used for all potential classifier and reference genes. Genes of interest (known to be upregulated in hypoxic tumors and associated with tumors most likely to progress) included the following: ADM (stress response), ALDOA (glucose metabolism), ANKRD37 (protein-protein interactions), BNIP3 (apoptosis), BNIP3L (apoptosis), C3orf28 (unknown), EGNL3 (regulation of HIF-1 activity), KCTD11 (apoptosis), LOX (extracellular matrix metabolism), NDRG1 (stress response), P4HA1 (extracellular-matrix metabolism). P4HA2 (extracellular matrix metabolism), PDK1 (energy metabolism), PFKFB3 (glucose metabolism) and SLC2A1 (glucose metabolism). Assay of gene expression in the tumor xenografts from the animals treated with DDFPe showed significantly lower expression of the hypoxia related genes than in tumor tissue specimen derived from the animals treated with saline control injections.

Prophetic Example 12

The following prophetic example is meant to show how administration of DDFPe can downregulate expression of genes that are over expressed in hypoxic tumor tissue and upregulate expression of genes that are expressed in normoxic tissue (i.e. normalize gene expression). Fischer 344 rats (F344/Ncr; National Cancer Institute, Frederick, Md.) were used to generate 9 L glioma tumor models. Pieces of 9 L glioma were tied into the epigastric artery/epigastric vein pair as previously described. The animals received daily IV injections of either 0.45 cc/kg DDFPe or saline until the tumors weighed approximately 1.5-g at which time the animals were euthanized, the tumors removed and flash frozen. Gene expression in the tumors was assayed similarly to that described above. Up-regulated genes seen in the control group included BCL2/adenovirus EIB 19 kDa-interacting protein 3, homo oxygenase (decycling) 1, activating transcription factor 3, heat shock protein (HSP27), N-myc downstream regulated gene 1, carbonic anhydrase 9 and others. Genes that were downregulated in the control group included Ly6-C antigen, solute carrier family 44 (member2), sterile alpha motif domain containing 9-like, DEAD (Asp-Glu-Ala-Asp) box polypeptide 60 and CD3 molecule delta polypeptide and others. Comparison of gene expression from 9-L glioma tissues from the animals treated with DDFPe showed significant decrease in expression of the genes that were upregulated in the control animals and significant increase in the genes that were downregulated in the control animals; i.e. there was normalization of gene expression in the tumors from animals treated with DDFPe. See, Marotta, Diane, et al. "In vivo profiling of hypoxic gene expression in gliomas using the hypoxia marker EF5 and laser-capture microdissection." Cancer research 71.3 (2011): 779-789.

Prophetic Example 13

A 30% sucrose solution was prepared as described in example 1. In a second vessel a suspension of a mixture of phospholipids with the following composition. DPPC and DPPE-PEG 5 k in a mole ratio of 92% DPPC and 8 mole percent DPPE-PEG was prepared by warming them in water to above the phase transition temperature of the all the lipids. Once the lipids were dispersed the suspension was cooled to 4 C. and stirred in a jacketed vessel. Pre-cooled (4° C.) DDFP was added to the stirred phospholipid suspension at weight ratio of 7 to 1, and allowed to stir until a uniformly milky suspension was achieved. This suspension was homogenized under high pressure in an Avestin model C50 homogenizer for up to 18 minutes keeping the temperature below 7° C. The emulsion was transferred via the homogenizer under low pressure to a vessel containing 30% sucrose solution in water; the resulting solution is stirred for up to 20 minutes, and then transferred through the homogenizer under low pressure to a second vessel. This solution was then transferred through a 0.2 micron filter into a third vessel. The product was dispensed to vials, which were capped and crimped. These operations were carried out at <8° C. in cold jacketed vessels due to the volatility of the active ingredient (DDFP). Compensation for losses during processing are accounted for by the use of an overage of the active component. Product fill volume was also tightly controlled to produce vials to meet release and shelf-life specifications.

Prophetic Example 14

A 30% sucrose solution was prepared as described in example 1. In a second vessel a suspension of a mixture of phospholipids with the following composition, DPPC and DPPE-PEG 5 k was prepared by warming them in water to above the phase transition temperature of the all the lipids. Once the lipids are dispersed the suspension was cooled to 4° C. and stirred in a jacketed vessel. Pre-cooled (4° C.) perfluorohexane was added to the stirred phospholipid suspension at weight ratio of 7 to 1, and allowed to stir until a uniformly milky suspension was achieved. This suspension was homogenized under high pressure in an Avestin model C50 homogenizer for up to 18 minutes keeping the temperature below 7° C.). The emulsion was transferred via the homogenizer under low pressure to a vessel containing 30% sucrose solution in water, the resulting solution was stirred for up to 20 minutes, and then transferred through the homogenizer under low pressure to a second vessel. This solution was then transferred through a 0.2 micron filter into a third vessel. The product was dispensed to vials, which were capped and crimped. These operations were carried out at <8° C. in cold jacketed vessels due to the volatility of the active ingredient (perfluorohexane). Compensation for losses during processing were accounted for by the use of an overage of the active component. Product fill volume was also tightly controlled to produce vials to meet release and shelf-life specifications.

Prophetic Example 15

A 30% sucrose solution was prepared as described in example 1. In a second vessel a suspension of a mixture of phospholipids with the following composition, DPPC, cholesterol and DPPE-PEG 5 k was prepared by warming them in water to above the phase transition temperature of the all the lipids. Once the lipids were dispersed the suspension was cooled to 4° C. and stirred in a jacketed vessel. Pre-cooled (4° C.) perfluoroheptane was added to the stirred phospholipid suspension at weight ratio of 7 to 1, and allowed to stir until a uniformly milky suspension was achieved. This suspension was homogenized under high pressure in an Avestin model C50 homogenizer for up to 18 minutes keeping the temperature below 7° C. The emulsion was transferred via the homogenizer under low pressure to a vessel containing 30% sucrose solution in water; the resulting solution was stirred for up to 20 minutes, and then transferred through the homogenizer under low pressure to a second vessel. This solution was then transferred through a 0.2 micron filter into a third vessel. The product was dispensed to vials, which were capped and crimped. These operations were carried out at <8° C. in cold jacketed vessels due to the volatility of the active ingredient (perfluoroheptane). Compensation for losses during processing were accounted for by the use of an overage of the active component. Product fill volume was also tightly controlled to produce vials to meet release and shelf-life specifications.

Prophetic Example 16

A 30% sucrose solution was prepared as described in example 1. In a second vessel a suspension of a mixture of phospholipids with the following composition, DPPC, phosphatidic acid (DPPA) and DPPE-PEG 5 k was prepared by warming them in water to above the phase transition temperature of the all the lipids. Once the lipids were dispersed the suspension was cooled to 4° C. and stirred in a jacketed vessel. Pre-cooled (4° C.) perfluorooctane was added to the stirred phospholipid suspension at weight ratio of 7 to 1, and allowed to stir until a uniformly milky suspension was achieved. This suspension was homogenized under high pressure in an Avestin model C50 homogenizer for up to 18 minutes keeping the temperature below 7° C. The emulsion was transferred via the homogenizer under low pressure to a vessel containing 30% sucrose solution in water; the resulting solution is stirred for up to 20 minutes, and then transferred through the homogenizer under low pressure to a second vessel. This solution was then transferred through a 0.2 micron filter into a third vessel. The product was dispensed to vials, which were capped and crimped. These operations are carried out at <8° C. in cold jacketed vessels due to the volatility of the active ingredient (perfluorooctane). Compensation for losses during processing were accounted for by the use of an overage of the active component. Product fill volume was also tightly controlled to produce vials to meet release and shelf-life specifications.

Prophetic Example 17

A suspension of a mixture of phospholipids with the following composition, dioleoylphosphatidylcholine (DOPC), cholesterol and dioleoylphosphatidylethanolamine-PEG-5,000 was prepared by warming them in water to above the phase transition temperature of the all the lipids. The resulting suspension of lipids was suspended in a mixture of propylene glycol/glycerol to achieve 80:10:10 weight percent phosphate buffered saline:propylene glycol:glycerol. Once the lipids were dispersed the suspension was cooled to 4 C and stirred in a jacketed vessel. Pre-cooled (4° C.) perfluorohexane was added to the stirred phospholipid suspension at weight ratio of 7 to 1, and allowed to stir until a uniformly milky suspension was achieved. This suspension was homogenized under high pressure in an Avestin model C50 homogenizer for up to 18 minutes keeping the temperature below 7° C. The emulsion was transferred via the homogenizer under low pressure to a vessel containing 30% sucrose solution in water; the resulting solution is stirred for up to 20 minutes, and then transferred through the homogenizer under low pressure to a second vessel. This solution was then transferred through a 0.2 micron filter into a third vessel. The product was dispensed to vials, which were capped and crimped. These operations are carried out at <8° C. in cold jacketed vessels due to the volatility of the active ingredient (perfluorooctane). Compensation for losses during processing were accounted for by the use of an overage of the active component. Product fill volume was also tightly controlled to produce vials to meet release and shelf-life specifications.

While the preferred embodiments of the present invention have been illustrated in detail, it should be apparent that modifications and adaptations to those embodiments may occur to one skilled in the art without departing from the scope of the present invention as set forth herein.

I claim:

1. A method of treating solid hypoxic tumors by multi-fraction radiotherapy, comprising administering to a subject suffering from a solid hypoxic tumor, concomitantly or up to 120 minutes prior to each fraction of radiation therapy, a water emulsion of perfluoropentane to the mammal, wherein
the perfluoropentane emulsion comprises a viscosity modifier, a fluorosurfactant, and about 1% to 10% w/vol of perfluoropentane, and
the solid hypoxic tumor is selected from pancreatic cancer, non-small cell lung cancer, cervical carcinoma, squamous cell carcinoma, ovarian cancer, sarcoma, multiple myeloma, prostate cancer, rectal cancer, Wilms tumor, head and neck cancer, oral carcinoma and uterine carcinoma.

2. The method of claim 1, wherein the subject is concomitantly administered a chemotherapeutic agent.

3. The method of claim 1, wherein the subject is concomitantly administered an immunosensitizing agent.

4. The method of claim 1, wherein the solid hypoxic tumor is pancreatic cancer.

5. The method of claim 1, wherein the solid hypoxic tumor is non-small cell lung cancer.

6. The method of claim 1, wherein the perfluoropentane emulsion comprises about 1% to 5% w/vol of perfluoropentane.

7. The method of claim 6, wherein the perfluoropentane emulsion is administered at a dosage in the range from about 0.05 cc/kg to about 0.3 cc/kg.

8. The method of claim 7, wherein administration of the perfluoropentane emulsion is intravenous infusion for up to 30 minutes.

9. The method of claim 7, wherein administration of the perfluoropentane emulsion is intravenous infusion as a single bolus.

10. The method of claim 1, wherein the fluorosurfactant is PEG Telomer B.

11. The method of claim 10, wherein the fluorosurfactant is PEG Telomer B is present at about 3 mg/mL.

12. The method of claim 1, wherein the viscosity modifier comprises sucrose.

13. The method of claim 12, wherein the sucrose is present at about 300 mg/mL.

14. The method of claim 1, wherein the perfluoropentane emulsion is co-administered with an anticancer agent.

15. The method of claim 14, wherein the anticancer agent is an antibody.

16. The method of claim 1, wherein the subject is concomitantly administered a chemotherapeutic and an immunosensitizing agent.

\* \* \* \* \*